United States Patent
Lee et al.

(10) Patent No.: US 9,663,809 B2
(45) Date of Patent: May 30, 2017

(54) METHOD FOR PRODUCING RNA MEMBRANE AND RNA MEMBRANE PRODUCED THEREBY

(71) Applicant: UNIVERSITY OF SEOUL INDUSTRY COOPERATION FOUNDATION, Seoul (KR)

(72) Inventors: Jong-Bum Lee, Seoul (KR); Dae-Hoon Han, Namyangju-si (KR)

(73) Assignee: UNIVERSITY OF SEOUL INDUSTRY COOPERATION FOUNDATION, Seoul (KR)

(*) Notice: Subject to any disclaimer, the term of this patent is extended or adjusted under 35 U.S.C. 154(b) by 0 days.

(21) Appl. No.: 15/035,747

(22) PCT Filed: Nov. 18, 2014

(86) PCT No.: PCT/KR2014/011089
§ 371 (c)(1),
(2) Date: May 10, 2016

(87) PCT Pub. No.: WO2015/076545
PCT Pub. Date: May 28, 2015

(65) Prior Publication Data
US 2016/0281123 A1    Sep. 29, 2016

(30) Foreign Application Priority Data
Nov. 19, 2013 (KR) .................. 10-2013-0140334

(51) Int. Cl.
*C12N 15/11* (2006.01)
*C12P 19/34* (2006.01)
*C12N 15/10* (2006.01)

(52) U.S. Cl.
CPC .............. *C12P 19/34* (2013.01); *C12N 15/10* (2013.01); *C12N 15/1003* (2013.01)

(58) Field of Classification Search
None
See application file for complete search history.

(56) References Cited

PUBLICATIONS

Lee et al (Nature Materials 11:316-323, Apr. 1, 2012).*
Lee et al (Nature Materials 11, Supplementary Information, Apr. 1, 2012).*
Hoshino et al. Preparations of a RNA-lipid complex film and its physical Properties, Nucleic Acids Research Supplement No. 1, pp. 61-62, 2001 Oxford University Press.

* cited by examiner

*Primary Examiner* — Richard Schnizer
(74) *Attorney, Agent, or Firm* — Goldilocks Zone IP Law (57) ABSTRACT

Disclosed are a method of manufacturing an RNA membrane and an RNA membrane manufactured thereby, wherein the RNA membrane can be produced at lower cost, in which the RNA membrane is composed exclusively of RNA, and thus has no toxicity in vivo, is controllable, and can be effectively applied to bio-organs such as the pericardium, as well as the production of peptides or proteins, and particularly, long linear RNA strands, which have not yet formed particles, are concentrated on the surface of a tube by inducing an evaporation process to thus activate the bonding of base pairs thereof, and the roughness and thickness of the RNA membrane can be controlled by changing the manufacturing conditions.

5 Claims, 11 Drawing Sheets
(4 of 11 Drawing Sheet(s) Filed in Color)

METHOD FOR PRODUCING RNA MEMBRANE AND RNA MEMBRANE PRODUCED THEREBY

CROSS-REFERENCE TO RELATED APPLICATIONS

This application claims the benefit under 35 U.S.C. Section 371, of PCT International Application No.: PCT/KR/KR2014/011089, filed on Nov. 18, 2014, which claims foreign priority to Korean Patent Application No.: KR10-2013-014033410, filed on Nov. 19, 2013, in the Korean Intellectual Property Office, both of which are hereby incorporated by reference in their entireties.

TECHNICAL FIELD

The present invention relates to a method of manufacturing an RNA membrane and an RNA membrane manufactured thereby, wherein the RNA membrane may be produced at lower cost, in which the RNA membrane is composed exclusively of RNA, and thus has no toxicity in vivo, is controllable, and may be effectively applied to bio-organs such as the pericardium, as well as the production of peptides or proteins. More particularly, the present invention relates to a method of manufacturing an RNA membrane and an RNA membrane manufactured thereby, wherein long linear RNA strands, which have not yet formed particles, are concentrated on the surface of a tube by inducing an evaporation process so as to activate the bonding of base pairs thereof, and wherein the roughness and thickness of the RNA membrane may be controlled by changing the manufacturing conditions.

BACKGROUND ART

DNA and RNA are biomaterials, and are advantageous because they have no toxicity in vivo, and may be freely controlled on the nano scale using base pair bonds. Many techniques using DNA have been developed, and thorough research into DNA is ongoing.

RNA may play a more important role in transferring genetic information than DNA, but RNA is easily degraded and is expensive to synthesize compared to DNA, and thus limitations are imposed on research and development thereof.

(Paper Literature)

"Preparations of a RNA-lipid complex film and its physical properties" (2001 Oxford University Press, Nucleic Acids Research Supplement No. 1 61-62, Yu Hoshino et al.)

The RNA film disclosed in the above (Paper Literature) is made up of RNA by mixing RNA, extracted from yeast, with a cation material, but is disadvantageous because it is not composed exclusively of RNA but further includes the cation material, and is thus unsuitable for use in medical applications. Furthermore, complicated processes are required to extract RNA from yeast, undesirably increasing manufacturing costs.

Despite the advantages of RNA, research and development aimed at improving existing methods of manufacturing a membrane comprising RNA has been limited due to excessively high RNA synthesis costs, and it is difficult to obtain a membrane composed exclusively of RNA. Hence, the need for a novel production method that is able to solve such problems comes to the fore.

DISCLOSURE

Technical Problem

Accordingly, the present invention has been made keeping in mind the above problems encountered in the related art, and an object of the present invention is to provide a method of manufacturing an RNA membrane and an RNA membrane manufactured thereby, wherein the RNA membrane may be produced at lower cost, in which the RNA membrane is composed exclusively of RNA and thus has no toxicity in vivo, is controllable, may be effectively applied to bio-organs, such as the pericardium, as well as the production of peptides or proteins, and may be utilized in drug delivery.

Another object of the present invention is to provide a method of manufacturing an RNA membrane and an RNA membrane obtained thereby, wherein the RNA membrane may be separated after the reaction due to its macroscopic size, and may thus be re-used and may be stably stored for a long period of time.

Still another object of the present invention is to provide a method of manufacturing an RNA membrane and an RNA membrane obtained thereby, wherein long linear RNA strands, which have not yet formed particles, are concentrated on the surface of a tube by inducing an evaporation process, thereby enabling the effective bonding of base pairs.

Yet another object of the present invention is to provide a method of manufacturing an RNA membrane and an RNA membrane obtained thereby, wherein the roughness and thickness of the RNA membrane may be controlled by changing the manufacturing conditions.

Technical Solution

In order to accomplish the above objects of the present invention, a method of manufacturing an RNA membrane and an RNA membrane obtained thereby have the following constructions.

An embodiment of the present invention provides a method of manufacturing an RNA membrane, comprising: a first circular DNA production step of producing first circular DNA; a second circular DNA production step of producing second circular DNA having a base sequence complementary to that of the first circular DNA; a first linear RNA production step of producing first linear RNA using the first circular DNA through transcription; a second linear RNA production step of producing second linear RNA using the second circular DNA through transcription; and an RNA membrane production step of producing an RNA membrane by inducing bonding of base pairs of the first linear RNA and the second linear RNA.

In another embodiment of the present invention, the RNA membrane production step may include an evaporation step of concentrating long linear RNA strands, which have not yet formed particles, through evaporation, thus activating bonding of base pairs of the RNA strands.

In still another embodiment of the present invention, the evaporation step may be performed by removing a cover from a tube in which the RNA membrane is produced to induce evaporation, whereby the long linear RNA strands, which have not yet formed particles, are concentrated on a surface of the tube and the bonding of the base pairs thereof is actively carried out.

In yet another embodiment of the present invention, the RNA membrane production step may further include a membrane roughness control step of controlling a roughness of the RNA membrane by adjusting the number of base pairs that are bonded between the first linear RNA and the second linear RNA.

In still yet another embodiment of the present invention, the RNA membrane production step may further include a membrane thickness control step of controlling a thickness of the RNA membrane by adjusting the concentration of the first circular DNA and the second circular DNA.

A further embodiment of the present invention provides an RNA membrane, manufactured by the method as described above.

Advantageous Effects

According to the present invention, the following effects can be attained in conjunction with the above embodiments and the constructions below.

In the present invention, the RNA membrane can be produced at lower cost, in which the RNA membrane is composed exclusively of RNA and thus has no toxicity in vivo, is controllable, can be effectively applied to bio-organs, such as the pericardium, as well as the production of peptides or proteins, and can be utilized in drug delivery.

In the present invention, the RNA membrane can be separated after the reaction due to its macroscopic size, and can thus be re-used and can be stably stored for a long period of time.

In the present invention, long linear RNA strands, which have not yet formed particles, can be concentrated on the surface of a tube by inducing an evaporation process, thereby enabling the effective bonding of base pairs.

In the present invention, the roughness and thickness of the RNA membrane can be controlled by changing the manufacturing conditions.

DESCRIPTION OF DRAWINGS

The patent or application file contains at least one drawing executed in color. Copies of this patent or patent application publication with color drawing(s) will be provided by the Office upon request and payment of the necessary fee.

BEST MODE

Hereinafter, a detailed description will be given of a method of manufacturing an RNA membrane and an RNA membrane manufactured thereby according to preferred embodiments of the present invention, with reference to the appended drawings. In the following description of the present invention, detailed descriptions of known functions and components incorporated herein will be omitted when it may make the subject matter of the present invention unclear. As used herein, when any part "includes" any element, it means that other elements are not precluded but may be further included, unless otherwise mentioned.

With reference to FIGS. 1 to 14, the method of manufacturing the RNA membrane according to an embodiment of the present invention includes: a first circular DNA production step (S1) of producing first circular DNA 11; a second circular DNA production step (S2) of producing second circular DNA 12 having a base sequence complementary to that of the first circular DNA 11; a first linear RNA production step (S3) of producing first linear RNA 21 using the first circular DNA 11 through transcription; a second linear RNA production step (S4) of producing second linear RNA 22 using the second circular DNA 12 through transcription; and an RNA membrane production step (S5) of producing an RNA membrane by inducing bonding of base pairs of the first linear RNA 21 and the second linear RNA 22.

RCT (Rolling Circle Transcription) is a process of producing long RNA strands from circular DNA using an RNA polymerase, thus enabling the production of a large amount of RNA at low cost because RNA strands complementary to the base sequence of circular DNA are continuously produced by means of the RNA polymerase. Furthermore, the reaction temperature is constant, at 37° C., and thus the reaction is simple and economical. Accordingly, in the present invention, RNA strands are produced using RCT, and are then employed in the manufacture of an RNA membrane.

Figure 1:
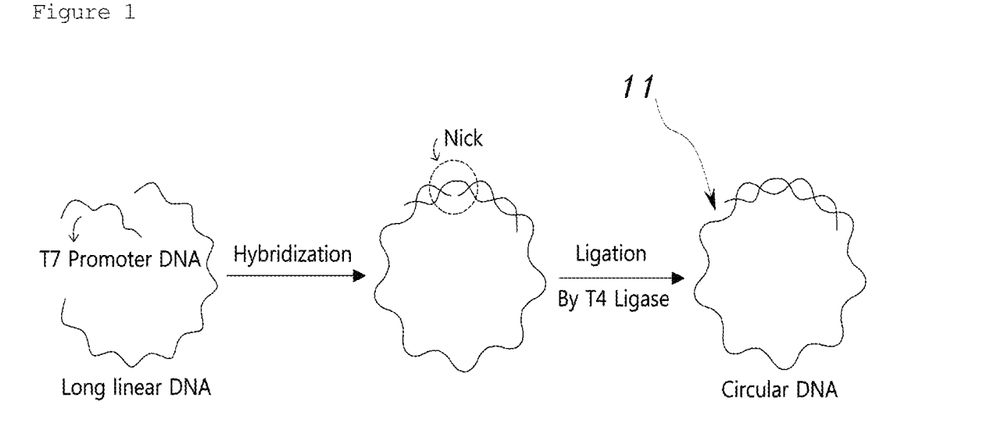
FIG. 1 illustrates the process of producing first circular DNA.

In the first circular DNA production step (S1) of producing the first circular DNA 11, a circular DNA structure is formed using two kinds of DNA. With reference to FIG. 1, long linear DNA and T7 Promoter DNA are subjected to hybridization and ligation, resulting in the circular DNA structure, that is, the first circular DNA 11.

In the second circular DNA production step (S2) of producing the second circular DNA 12, a circular DNA structure, i.e. second circular DNA 12, is produced using two kinds of DNA, according to the same principle and in the same manner as in the first circular DNA production step (S1). The second circular DNA 12 is circular DNA having a base sequence complementary to the base sequence of the first circular DNA 11.

Figure 2:
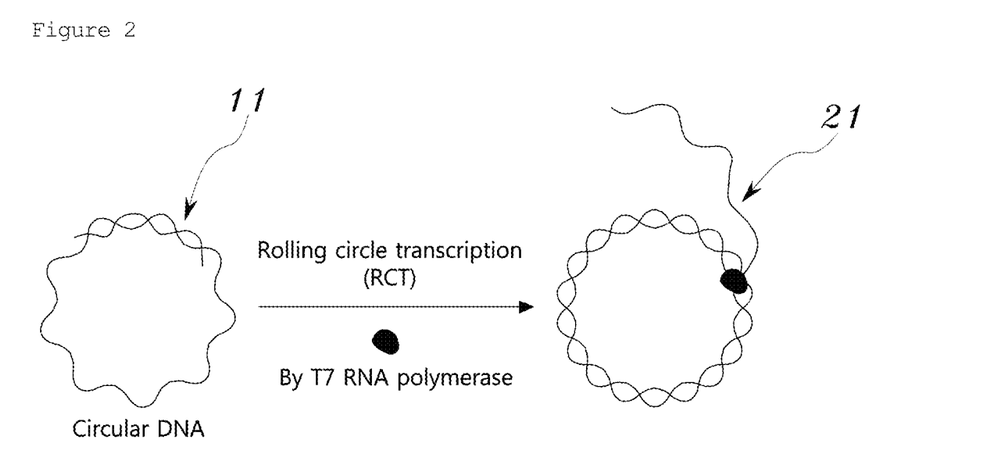
FIG. 2 illustrates the process of producing first linear RNA.

In the first linear RNA production step (S3), the first linear RNA 21 is produced using the first circular DNA 11 through transcription. With reference to FIG. 2, the first circular DNA 11 produced in the first circular DNA production step (S1) is subjected to transcription using a T7 RNA polymerase, thereby producing long-stranded first linear RNA 21 complementary to the base sequence of the first circular DNA 11.

In the second linear RNA production step (S4), the second linear RNA 22 is produced using the second circular DNA 12 according to the same principle and in the same manner as in the first linear RNA production step (S3). The second circular DNA 12 produced in the second circular DNA production step (S2) is subjected to transcription using the T7 RNA polymerase, thereby producing long-stranded second linear RNA 22 complementary to the base sequence of the second circular DNA 12.

Figure 3:
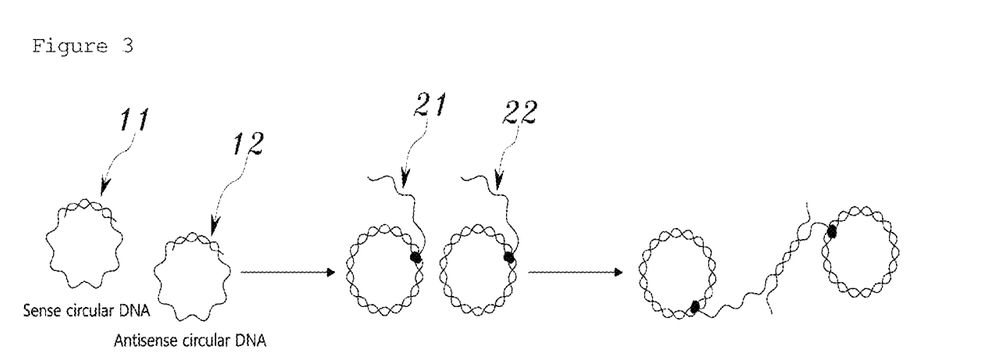
FIG. 3 illustrates the process of producing an RNA membrane.
Figure 4:
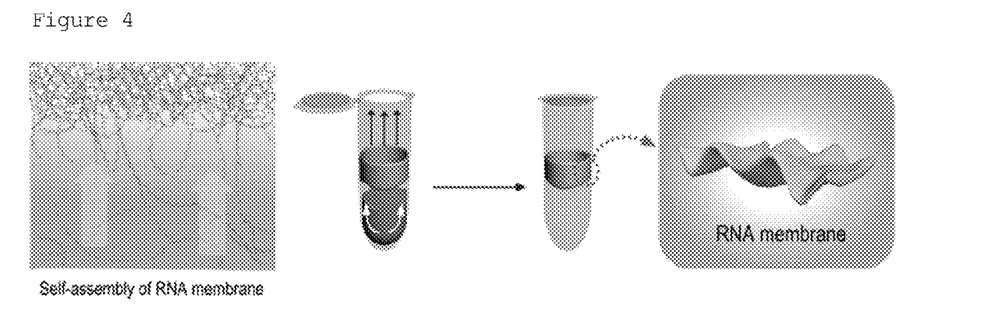
FIG. 4 illustrates the evaporation process.

In the RNA membrane production step (S5), bonding of base pairs of the first linear RNA 21 and the second linear RNA 22 is induced, thereby producing the RNA membrane. With reference to FIG. 3, bonding of base pairs is carried out between the first linear RNA 21 obtained in the first linear RNA production step (S3) and the second linear RNA 22 obtained in the second linear RNA production step (S4), resulting in the RNA membrane. The RNA membrane is produced based on the main principle whereby the RNA strands are produced through transcription using two kinds of circular DNA and bonding of the base pairs thereof is induced. As such, the RNA membrane production step (S5) includes an evaporation step (S51) (EISA: Evaporation-Induced Self-Assembly, in which RNA strands present in the solution are concentrated on the surface of a tube and the concentrated RNA strands are bonded to the initially produced RNA membrane to form an RNA membrane having a larger size). The long strands of the first linear RNA 21 and the second linear RNA 22 are self-twisted and self-entangled to thus form micro-sized particles, which are then precipitated to the bottom of a tube (a container) in which the process of manufacturing the RNA membrane is carried out. In the evaporation step (S51), the long linear RNA strands, which have not yet formed particles, are concentrated through evaporation, thereby activating the bonding of base pairs of the RNA strands. With reference to FIG. 4, the long linear RNA strands, which have not yet formed the particles, are concentrated on the surface of the tube through the evaporation step (S51). As such, the bonding of base pairs of the RNA strands is actively carried out, resulting in the RNA membrane.

In the evaporation step (S51), when the volume of the solution in the tube where the RNA membrane is produced is large, the cover is removed from the tube, and evaporation of the solution is induced, taking care to prevent pollution of the solution (preferably, the temperature of 37° C. is maintained for about 24 hr under the condition that the tube is opened). Thereby, while the long linear RNA strands, which have not yet formed the particles, are concentrated on the surface of the tube, bonding of the base pairs is actively carried out.

Below is a description of the results of various tests for evaluating the production, morphology and properties of the RNA membrane according to the present invention.

Figure 5:
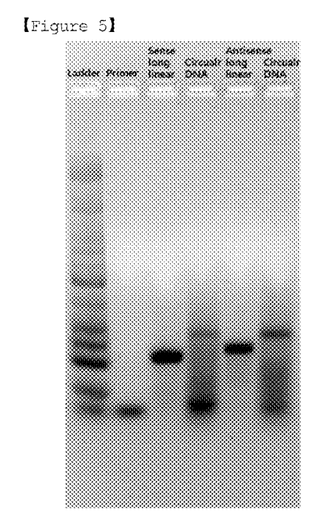
FIG. 5 is an image illustrating the results of electrophoresis testing.

Specifically, in order to evaluate whether circular DNA was formed well through the first circular DNA production step (S1) and the second circular DNA production step (S2), electrophoresis was performed. Since DNA has a strong negative charge, it moves toward the positive charge in the gel through electrophoresis, and is classified depending on the molecular weight thereof. The circular DNA is produced through ligation of two DNA strands, and thus the molecular weight thereof is increased, from which whether the circular DNA is effectively manufactured may be checked. The results are shown in FIG. 5.

Figure 6:
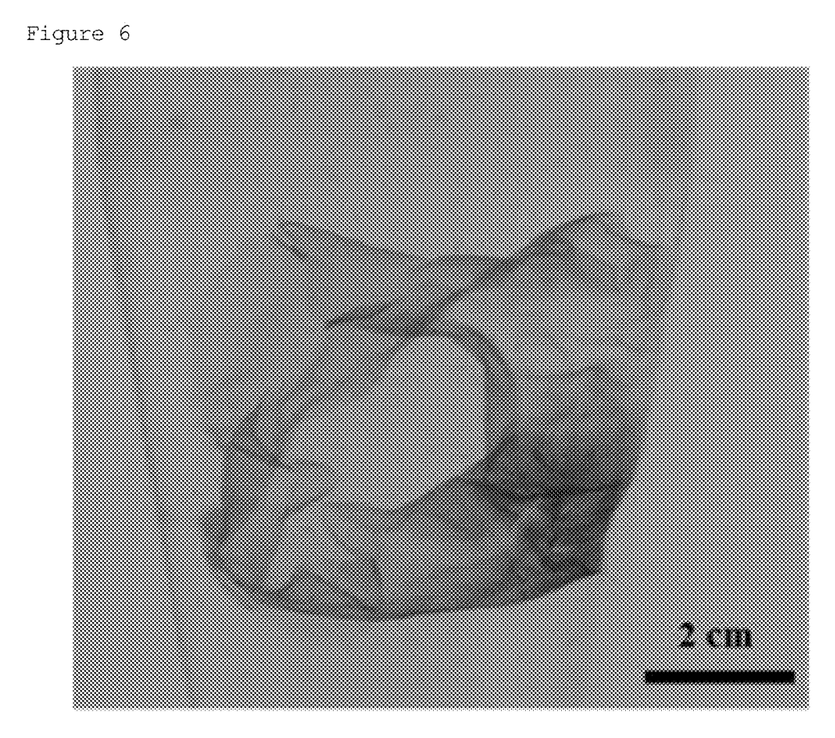
FIG. 6 is an image illustrating the results of staining of the RNA membrane.

Also, in order to evaluate the outer appearance of the RNA membrane according to the present invention, the RNA membrane was stained with GelRed for staining RNA. As illustrated in FIG. 6, the RNA membrane made in the tube had a hollow cylindrical shape, matching the internal shape of the tube. Furthermore, the RNA membrane composed of RNA can be seen to emit strong red fluorescence upon irradiation with UV light.

Figure 7:
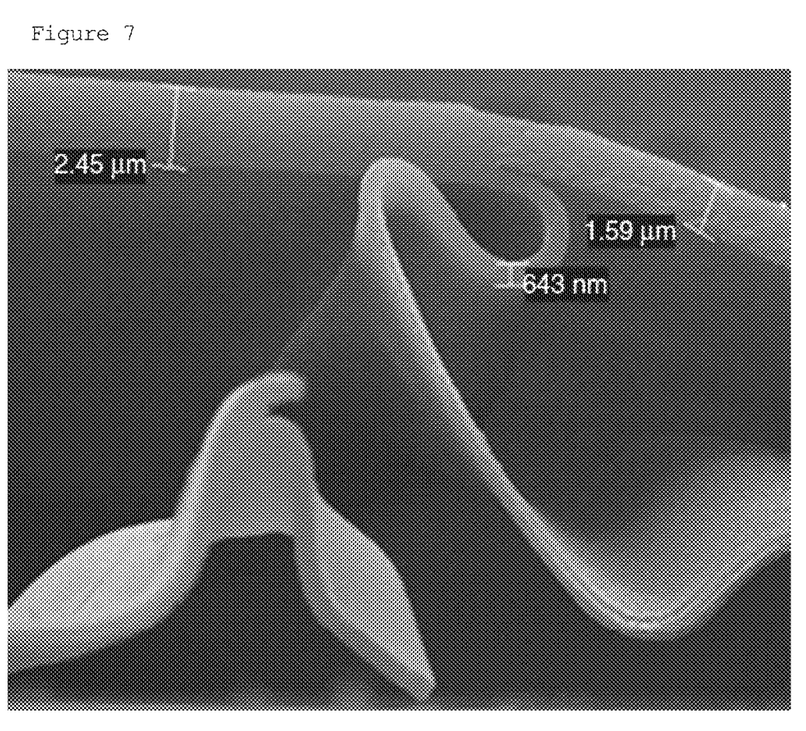
FIG. 7 illustrates the scanning electron microscopy (SEM) image of the surface of the RNA membrane.
Figure 8:
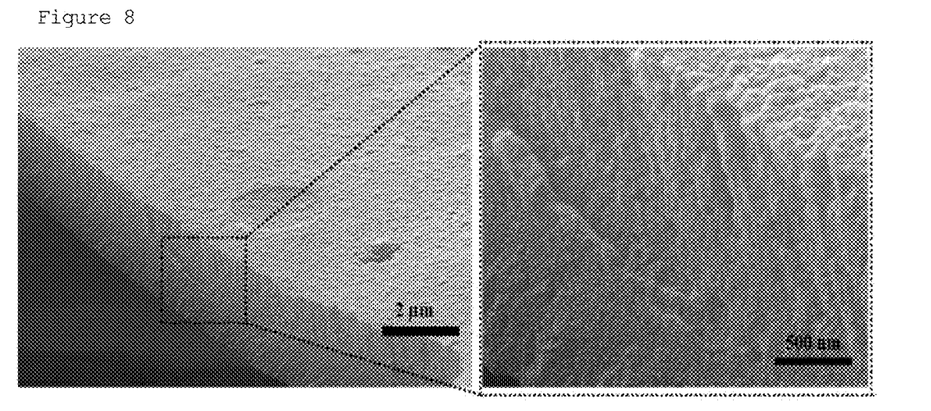
FIG. 8 illustrates the SEM images of the inside of the RNA membrane.

Also, in order to evaluate the surface and properties of the RNA membrane according to the present invention, SEM was performed. As illustrated in FIG. 7, the produced RNA membrane had a micro-sized thickness, and was able to be divided into a plurality of nano-sized layers. Moreover, as illustrated in FIG. 8, the RNA membrane was configured such that the inside thereof was very compact.

Figure 9:
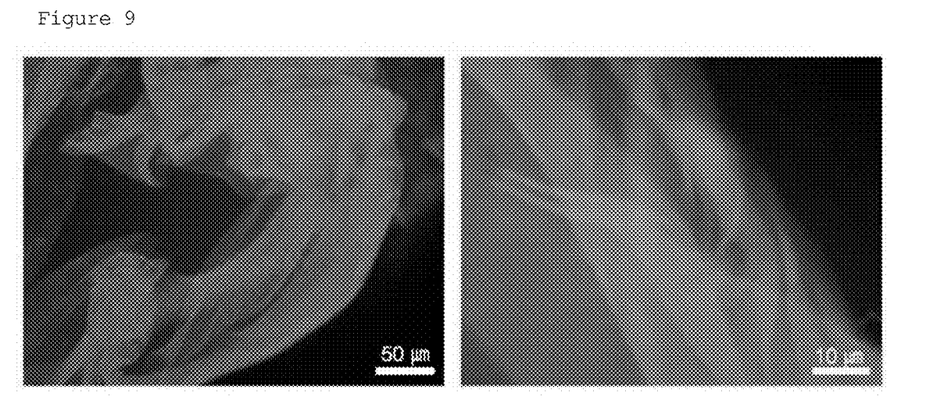
FIGS. 9 and 10 illustrate the fluorescence microscopy images of the RNA membrane.
Figure 10:
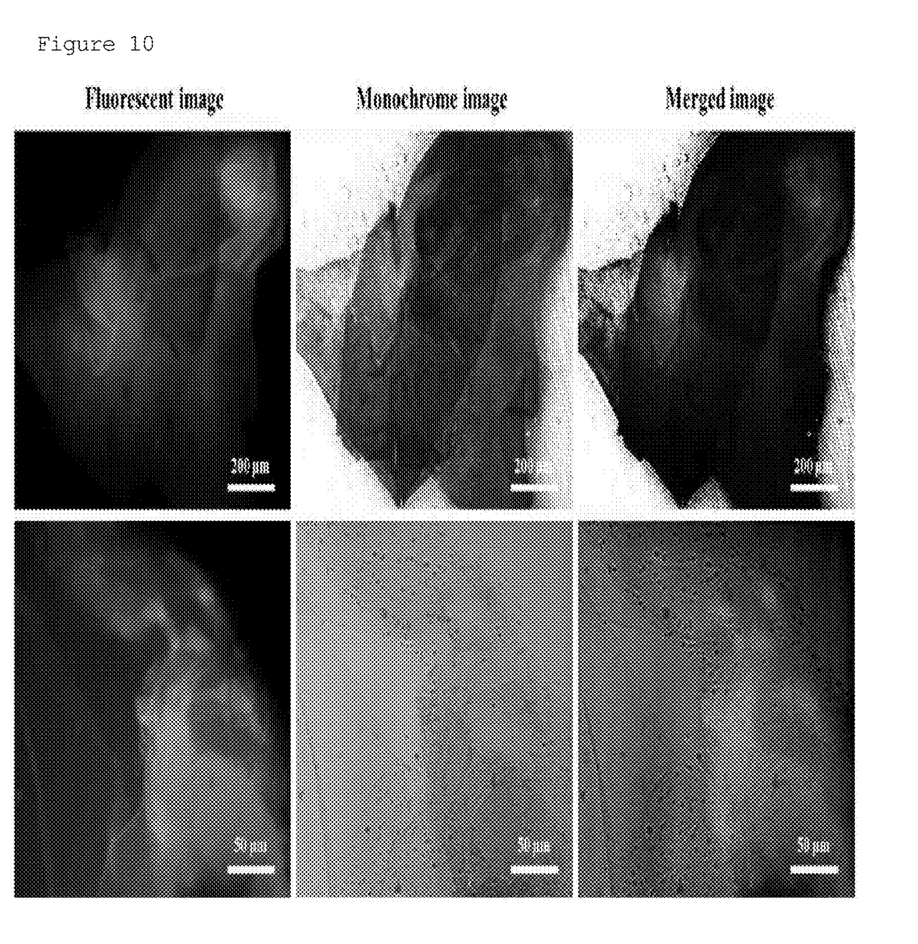

Also, the RNA membrane according to the present invention was stained with RNA fluorescence dyes, i.e. GelRed and SYBR Green II, and observed through fluorescence microscopy. The results are shown in FIGS. 9 and 10. As seen in FIGS. 9 and 10, the red stained portion was due to GelRed, and the green stained portion was due to SYBR Green II.

Figure 11:
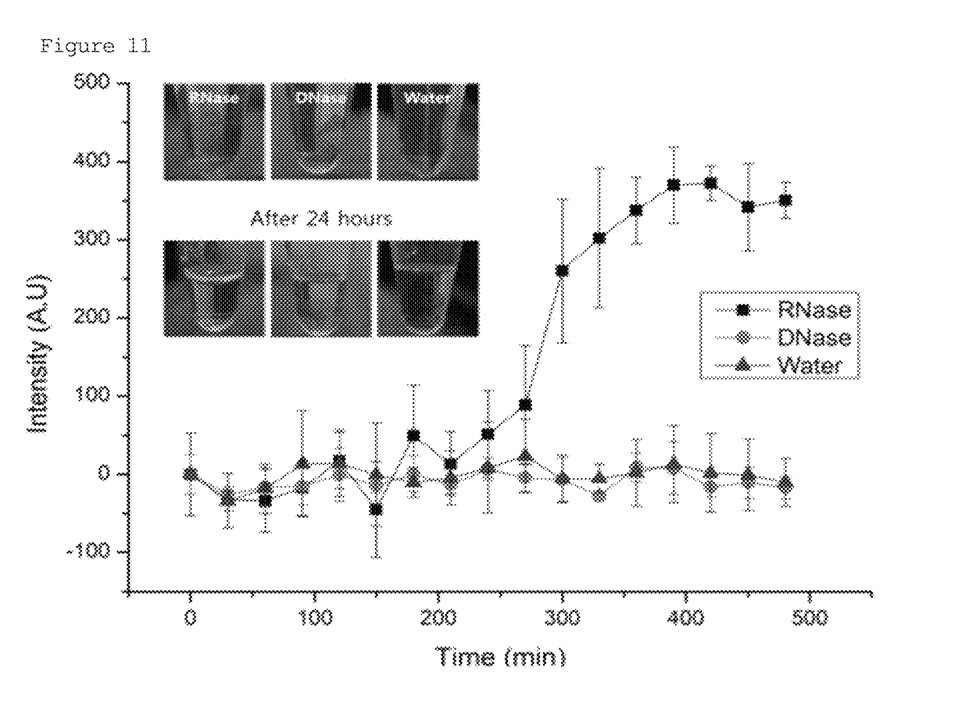
FIG. 11 is a graph illustrating the results of degradation of the RNA membrane.

Meanwhile, the RNA membrane according to the present invention is a membrane composed exclusively of RNA. Thus, its morphology may be stably maintained in the absence of an RNase (an enzyme that degrades RNA). To this end, the following three degradation tests (in the presence of RNase, in the presence of only DNase [an enzyme that degrades DNA], and in the absence of any degradation enzyme) were performed. As illustrated in FIG. 11, in the presence of RNase, the RNA membrane was completely degraded and GelRed RNA dye was distributed in the solution. However, the RNA membrane maintained its morphology in the other two tests, that is, in the presence of only the DNase and in the absence of any degradation enzyme. Even when the concentration of the DNase was 10 times higher than that of the RNase, the morphology of the RNA membrane was retained in the presence of the DNase. In order to obtain more reliable results, the intensity of fluorescence of each solution was measured using a microplate reader and plotted. Based on the measurement results, the fluorescence intensity was significantly increased only in the presence of RNase (FIG. 11).

Figure 12:
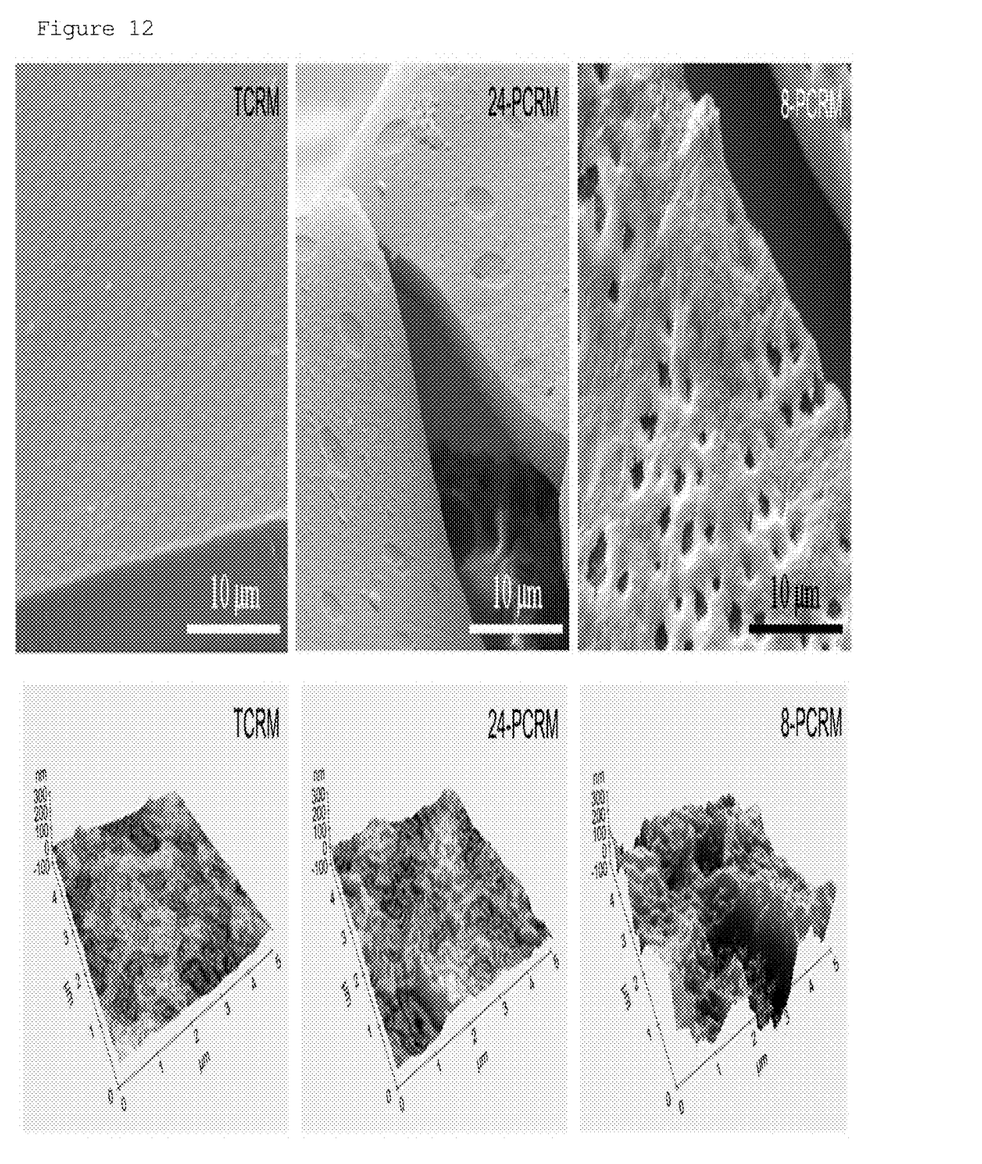
FIG. 12 illustrates the SEM and atomic force microscopy (AFM) images of the surface of the RNA membrane.

In the present invention, the RNA membrane production step (S5) may further include a membrane roughness control step (S53) of controlling the roughness of the RNA membrane by adjusting the number of base pairs that are bonded between the first linear RNA 21 and the second linear RNA 22. As the membrane roughness control step (S53) is additionally implemented in the present invention, the roughness of the RNA membrane may be controlled by adjusting the number of base pairs that are bonded between the first linear RNA 21 and the second linear RNA 22. FIG. 12 illustrates the SEM and AFM images of the surface of the RNA membrane resulting from adjusting the number of base pairs that are bonded in the membrane roughness control step (S53) (the number of bonded base pairs: 71 base pairs (TCRM)>24 base pairs (24-PCRM)>8 base pairs (8-PCRM)). Thereby, the surface of the RNA membrane can be seen to be smoother in proportion to the increase in the number of base pairs that are bonded.

Figure 13:
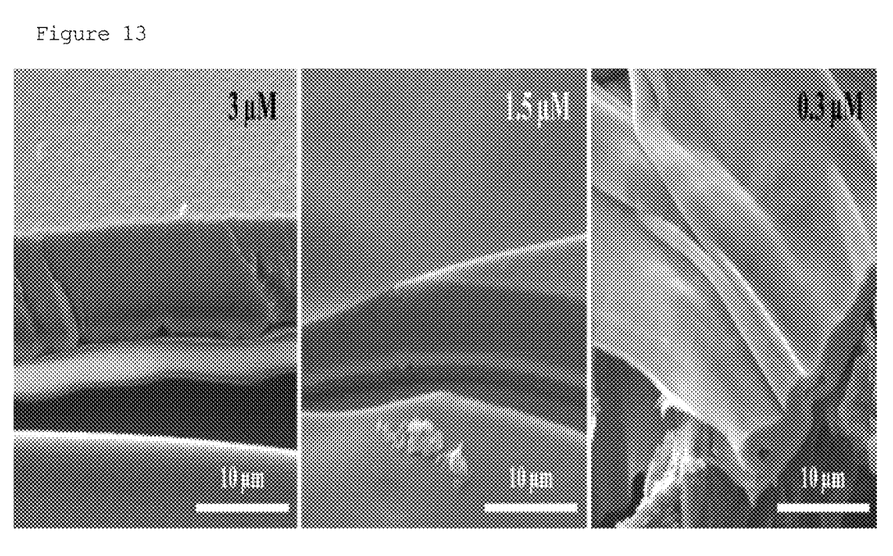
FIG. 13 illustrates the SEM images of the RNA membrane.

Also, the RNA membrane production step (S5) may further include a membrane thickness control step (S55) of controlling the thickness of the RNA membrane by adjusting the concentration of the first circular DNA 11 and the second circular DNA 12. As the membrane thickness control step (S55) is additionally implemented in the present invention, the concentration of the newly produced first circular DNA 11 and second circular DNA 12 are adjusted, thus controlling the thickness of the RNA membrane. FIG. 13 illustrates the SEM images of the RNA membrane obtained by adjusting the concentration of the newly produced first circular DNA 11 and second circular DNA 12 through the membrane thickness control step (S55). Consequently, the RNA membrane can be seen to be thinner in proportion to the decrease in the concentration of the newly produced circular DNA. Thus, it is possible to adjust the micro size of the RNA membrane obtained through the membrane thickness control step (S55).

The RNA membrane produced by the method of the present invention is composed exclusively of RNA, and thus has no toxicity in vivo, is controllable, and may be effectively utilized in bio-organs such as the pericardium as well as the production of peptides or proteins. In particular, the RNA membrane is useful in drug delivery with the addition of a drug to the RNA membrane.

Figure 14:
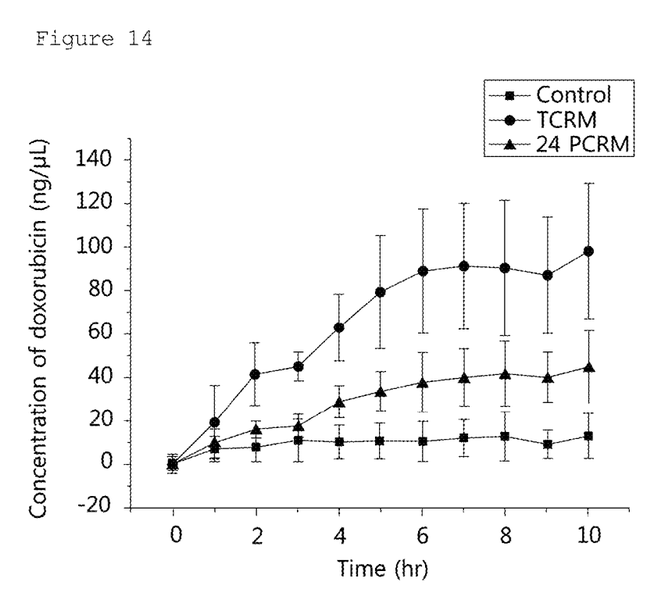
FIG. 14 is a graph illustrating the results of measurement of the drug delivery capability of the RNA membrane.

Below, the drug delivery capability of the RNA membrane according to the present invention was tested. In this test, whether a doxorubicin drug contained in the RNA membrane was distributed in the solution was checked in order to confirm the usefulness of the RNA membrane as a drug delivery vehicle. Specifically, TCRM (an RNA membrane comprising 71 base pairs) and 24-PCRM were placed in an RNase solution and incubated at 37° C. for 24 hr. In order to check whether the drug was delivered to the solution, the fluorescence of the solution was measured using a microplate reader. The results are shown in FIG. 14. In FIG. 14, the line marked "Control" shows the results when TCRM is added not to the RNase solution but to nuclease-free water. Thereby, TCRM and 24-PCRM can be evaluated to effectively deliver doxorubicin in the presence of RNase.

Also, the RNA membrane according to the present invention may shrink or expand depending on the presence or absence of moisture in the RNA membrane, and is thus easy to manufacture as a drug. When the RNA membrane is provided inside the solution, the RNA membrane formed in the tube according to the present invention has the same shape as in the inner surface of the tube. On the other hand, when the RNA membrane is provided outside the solution, moisture escapes from the membrane, and thus the membrane may shrink and assume the form of a stick. However, when the membrane is placed in the solution again, it expands again. Hence, the RNA membrane according to the present invention, having such properties, may be useful in a wider variety of applications.

In this way, since the RNA membrane according to the present invention is composed exclusively of RNA, it has no toxicity and is controllable, and may thus be applied in a variety of fields. Compared to conventional RNA direct synthesis methods, the RNA membrane of the invention may be produced at low cost, thus generating economic benefits. In particular, based on the large size of the RNA membrane and the high concentration of RNA, the potential to apply the RNA membrane to siRNA delivery may be evaluated to be very high. Also, the RNA membrane is made of a biomaterial, and is controllable, and may thus be effectively used in bio-organs such as the pericardium. Compared to conventional chemical materials for use in bio-organs, RNA made of a biomaterial may be more safely used, as it lacks toxicity. Furthermore, the RNA membrane has a macroscopic size, unlike mRNA necessary for conventional protein production, and thus, it is separable and recyclable after the translation reaction, and exists in the form of a large structure, compared to conventional short RNA strands, and may thus be stably stored for a long period of time.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method of manufacturing an RNA membrane, comprising:
    a first circular DNA production step of producing a first circular DNA;
    a second circular DNA production step of producing a second circular DNA having a base sequence complementary to that of the first circular DNA;
    a first linear RNA production step of producing a first linear RNA using the first circular DNA through transcription;
    a second linear RNA production step of producing a second linear RNA using the second circular DNA through transcription;
    and an RNA membrane production step of producing an RNA membrane by inducing bonding of base pairs of the first linear RNA and the second linear RNA; wherein the RNA membrane production step comprises an evaporation step of concentrating long linear RNA strands, which have not yet formed particles, through evaporation, thus activating bonding of base pairs of the RNA strands.

2. The method of claim 1, wherein the evaporation step is performed by removing a cover from a tube in which the RNA membrane is produced to induce evaporation, whereby the long linear RNA strands, which have not yet formed particles, are concentrated on a surface of the tube and the bonding of the base pairs thereof is actively carried out.

3. The method of claim 1, wherein the RNA membrane production step further comprises a membrane roughness control step of controlling a roughness of the RNA membrane by adjusting a number of base pairs that are bonded between the first linear RNA and the second linear RNA.

4. The method of claim 1, wherein the RNA membrane production step further comprises a membrane thickness control step of controlling a thickness of the RNA membrane by adjusting a concentration of the first circular DNA and the second circular DNA.

5. An RNA membrane, manufactured by the method of claim 1.

* * * * *